United States Patent [19]

Sonoi et al.

[11] Patent Number: 5,808,132
[45] Date of Patent: Sep. 15, 1998

[54] α,α-BIS(TRIFLUOROMETHYL)ARYLACETIC ACID ESTER; ITS INTERMEDIATES FOR SYNTHESIS; AND PROCESS FOR PRODUCING THE SAME

[75] Inventors: Takehiro Sonoi; Toshimasa Sagawa, both of Kitaibaraki; Futoshi Masaki; Toshio Kubota, both of Hitachi, all of Japan

[73] Assignee: Nippon Mektron, Limited, Tokyo, Japan

[21] Appl. No.: 614,224

[22] Filed: Mar. 12, 1996

[30] Foreign Application Priority Data

Jun. 8, 1995 [JP] Japan ..................................... 7-166965
Jun. 8, 1995 [JP] Japan ..................................... 7-166966

[51] Int. Cl.$^6$ .......................... C07C 69/76; C07D 303/02
[52] U.S. Cl. .......................... 560/105; 560/100; 549/550; 549/532
[58] Field of Search .................................. 560/105, 100; 549/532, 550

[56] References Cited

PUBLICATIONS

Chem Abst 91: 56281 1978.
Aaron, C., et al., "The Resolution and Configuration of α–Substituted Phenylacetic Acids", *J. Org. Chem.*, 32, pp. 2797–2803, 1967.
Everett, T.S., et al., "Preparation of αTrifluoromethyl Esters from Melonic Esters," *J. Org. Chem.*, 49, pp. 3702–3706, 1984.
Muzard, M., et al., "Fluorinated Ketene Dithioacetals; 1, Preparation and Application to the synthesis of α–Trifluoromethylthiocarboxylic S–Esters and Aldehyde Derivatives", *Synthesis*, pp. 965–968, Oct. 1992.
Middleton, W.J., et al., "The Synthesis of Antiinflammatory α–(Trifluoromethyl) Arylacetic Acids", *Journal of Fluorine Chemistry*, 22, pp. 561–574, 1983.
"Spring Annual Meeting Preprints II", *The Chemical Society of Japan*, N.69, p., 1080, published Mar. 13, 1995 (ISSN 0285–7626).

*Primary Examiner*—Paul J. Killos
*Attorney, Agent, or Firm*—Kenyon & Kenyon

[57] ABSTRACT

Heptafluoroisobutenyl methyl ether having the following formula:

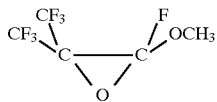

is oxidized with ozone to produce perfluoro(2-methyl-1,2-epoxy-propyl) methyl ether. The resulting intermediate compound is allowed to react with an aromatic compound ArH to produce α,α-bis(trifluoromethyl)arylacetic acid methyl ester having the following formula:

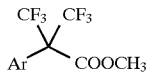

By hydrolysis, decarboxylation and further hydrolysis of the ester compound, α,α-bis(trifluoromethyl)arylacetic acid for use as raw materials for medicines, agricultural chemicals, liquid crystals, etc. or reagents for determining an optical purity can be obtained.

7 Claims, No Drawings

α,α-BIS(TRIFLUOROMETHYL)ARYLACETIC ACID ESTER; ITS INTERMEDIATES FOR SYNTHESIS; AND PROCESS FOR PRODUCING THE SAME

BACKGROUND OF THE INVENTION

1. Field of the Invention

The present invention relates to α,α-bis(trifluoromethyl)-arylacetic acid ester; its intermediates for synthesis; and a process for producing the same, and more particularly to α,α-bis(trifluoromethyl)arylacetic acid ester, which is effectively applicable as a raw material for synthesis of α-(trifluoromethyl)arylacetic acid; its intermediates for synthesis; and a process for producing the same.

2. Related Prior Art

α-(trifluoromethyl)arylacetic acid represented by the following general formula:

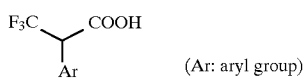

(Ar: aryl group)

can be produced according to the following conventional procedures:

(1) Journal of Organic Chemistry, vol.32, page 2797 (1967)

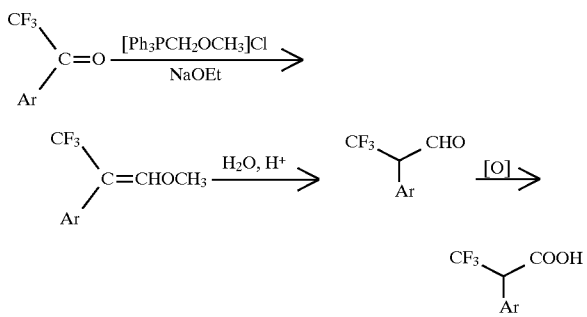

(2) Journal of Fluorine Chemistry, vol.22, page 561 (1983)

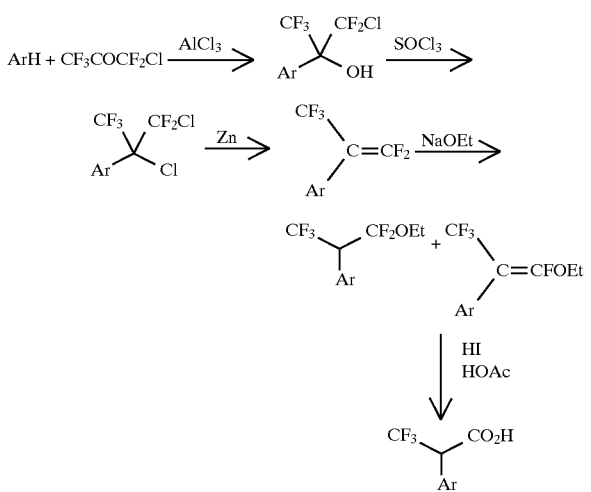

(3) Journal of Organic Chemistry, vol.49, page 3702 (1984)

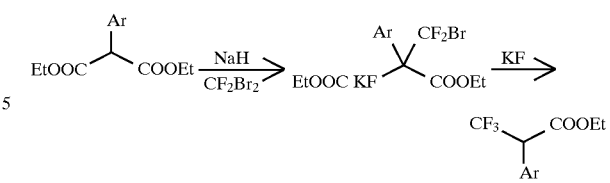

(4) Synthesis, vol.10, page 965 (1992)

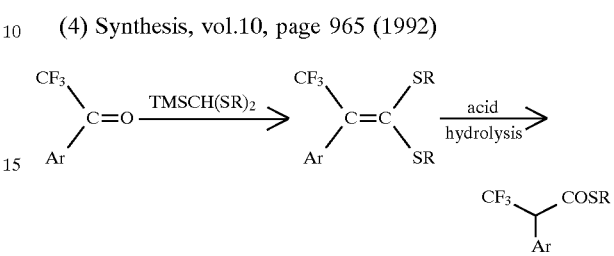

However, these procedures are not economically advantageous owing to expensive starting materials, necessity for a plurality of synthesis steps, difficulty in mass-production, etc.

SUMMARY OF THE INVENTION

An object of the present invention is to provide useful compounds as intermediates capable of economically producing α-(trifluoromethyl)arylacetic acid for use as raw materials for medicines, agricultural chemicals, liquid crystals, etc. or reagents for determining an optical purity, etc, and a process for producing the same.

DETAILED DESCRIPTION OF THE INVENTION

According to the present invention, an α,α-bis(trifluoromethyl)arylacetic acid ester, represented by the following general formula is provided:

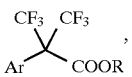

wherein Ar is an aryl group; R is a lower alkyl group, an aryl group or a benzyl group.

This compound can be obtained by the reaction of a perfluoro(2-methyl-1,2-epoxypropyl)ether compound, represented by the following general formula as a starting material:

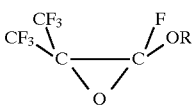

with an aromatic compound ArH.

Perfluoro(2-methyl-1,2-epoxypropyl)ether compound as the starting material can be prepared by oxidation of a heptafluoroisobutenyl ether compound, represented by the general formula $(CF_3)_2C=CF(OR)$, with ozone, and heptafluoroisobutenyl ether compound as a starting material for it can be readily obtained by addition reaction of octafluoroisobutene $(CF_3)_2C=CF_2$ with a lower alcohol, phenol, benzyl alcohol or the like, followed by dehydrofluorination reaction of the resulting addition reaction product $(CF_3)_2CHCF_2OR$ with potassium hydroxide or the like.

The oxidation reaction of heptafluoroisobutenyl ether compound with ozone is carried out in a glass reactor by charging the starting material and contacting it with an ozone-containing oxygen gas or air in the absence of a solvent or in the presence of such a solvent as hydrocarbon, halogenated hydrocarbon, ether or water with stirring at a temperature of about −70° C. to about 110° C., preferably about −40° C. to about 60° C. Ozone concentration in oxygen gas or air is not particularly limited, but generally is about 0.1 to about 1,000 mg/liter, preferably about 1 to 500 mg/liter. Molar ratio of ozone to the starting material for the oxidation reaction is about 1.

Epoxy group of the resulting perfluoro(2-methyl-1,2-epoxypropyl)ether compound has a very high activity and undergo cleavage easily in the presence or absence of a catalyst to react with an aromatic compound ArH, thereby forming an α,α-bis(trifluoromethyl)arylacetic acid ester.

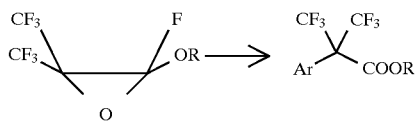

The aromatic compound ArH for this purpose includes, for example, aromatic hydrocarbons such as benzene, naphthalene, etc. and aromatic heterocyclic compounds such as pyrrole, pyridine, etc. and may have a lower alkyl group such as methyl, ethyl, isopropyl, t-butyl, etc. or a halogen such as chlorine, bromine, etc. as a substituent. The aromatic compound is used in large excess over the ether compound, generally in a molar ratio of the aromatic compound to the ether compound of about 1 to about 100, preferably about 1 to about 40.

The reaction of the ether compound with the aromatic compound is carried out in the presence or absence of a solvent. In the case of using a solvent, the species of the solvent is not limited, so long as it is inert to the ether compound and the aromatic compound, but it is preferable to use a solvent having a higher dissolvability. When an aromatic hydrocarbon is used as the aromatic compound in the reaction, it is preferable to use a catalyst. Preferable catalyst includes, for example, such Lewis acids as $AlCl_3$, $AlBr_3$, $ZnI_2$, $TiCl_4$, $SnCl_4$, $BF_3$, etc. The catalyst is used in a molar ratio of the catalyst to the ether compound of about 0.01 to about 10, preferably about 0.1 to about 3. The reaction temperature for this purpose is about −80° C. to about 200° C., preferably about −40° C. to about 100° C.

The α,α-bis(trifluoromethyl)arylacetic acid ester, as obtained as the result of reaction, can be converted to the corresponding carboxylic acid salt under the action of the base and water, followed by decarboxylation to form an olefinic compound, and further by hydrolysis to form an α-(trifluoro-methyl)arylacetic acid, as schematically given belows.

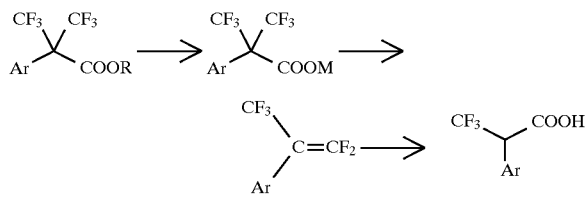

α-(trifluoromethyl)arylacetic acid can be readily produced through very simple reaction steps, that is by subjection a perfluoro(2-methyl-1,2-epoxypropyl)ether compound, which can be obtained by oxidation of heptafluoroisobutenyl ether compound with ozone, to reaction with an aromatic compound, thereby obtaining an α,α-bis(trifluoromethyl) arylacetic acid ester, followed by decarboxylation and hydrolysis.

PREFERRED EMBODIMENTS OF THE INVENTION

The present invention will be explained in detail below, referring to Examples and Reference Examples.

EXAMPLE 1

200 g (0.88 moles) of heptafluoroisobutenyl methyl ether (purity: 93%) was charged into a three-necked flask having a capacity of 300 ml, provided with a Dimroth condenser, a stirrer and a gas feed tube, and a brine at −20° C. was passed through the Dimroth condenser. About 340 liters of ozone-containing oxygen gas (ozone concentration: 125 mg/liter) was bubbled through the ether compound at 0° C. with stirring over 11 hours 18 minutes (total ozone amount: about 0.88 moles). After the reaction, 134.8 g of the reaction product was recovered therefrom and distilled, whereby 73.0 g of perfluoro(2-methyl-1,2-epoxypropyl) methyl ether was obtained as a fraction having a boiling point of 82° to 85° C. (yield: 36.5%).

Infrared absorption spectrum: 1230 $cm^{-1}$ (oxirane ring)
$^{19}F$-NMR (TFA, $CH_2Cl_2$):
−15.3 ppm (d, J=2.19 Hz, 1F)
+0.58 ppm (dq, J=2.19, 2.63 Hz, 3F)
+1.90 ppm (q, J=2.63 Hz, 3F)
$^1H$-NMR (TMS, $CDCl_3$):
3.58 ppm (s, 3H)
Mass spectrum (EI, M/Z): 228($M^+$)

EXAMPLE 2

6.67 g of anhydrous aluminum chloride and 50 ml of dry benzene were charged into a three-necked flask having a capacity of 300 ml, provided with a stirrer and a dropping funnel, and the flask was cooled to 0° C. Then, 11.4 g (0.05 moles) of perfluoro(2-methyl-1,2-epoxypropyl) methyl ether diluted with 30 ml of dry benzene was dropwise added into the flask with stirring. Reaction was carried out at room temperature for 10 hours while stirring, and then the reaction mixture was poured into ice water, and the separated organic layer was dried with anhydrous $MgSO_4$. The aqueous layer was extracted with dichloromethane, and the liquid extract was dried with anhydrous $MgSO_4$. These two organic layers were joined together and concentrated, and then the residue was distilled at a bath temperature of 120° to 130° C. under reduced pressure of 15 mmHg, whereby 10.05 g of methyl ester of α,α-bis-(trifluoromethyl)phenylacetic acid was obtained (yield: 70%).

Infrared absorption spectrum: 1810 $cm^{-1}$ (C=O)
$^{19}F$-NMR (TFA, $CH_2Cl_2$): +4.1 ppm (s)
$^1H$-NMR (TMS, $CDCl_3$):
3.7 ppm (s, 3H)
7.1 ppm (m, 5H)

EXAMPLE 3

2.67 g of anhydrous aluminum chloride and 10 ml of dry isobutylbenzene were charged into a three-necked flask having a capacity of 50 ml, provided with a stirrer and a dropping funnel, and then the flask was cooled to 0° C. Then, 4.56 g (0.02 moles) of perfluoro(2-methyl-1,2-epoxypropyl) methyl ether diluted with 2 ml of dry isobutylbenzene, was dropwise added into the flask with stirring. Reaction was carried out at room temperature for 10 hours, while stirring, and the reaction mixture was poured into ice water, and the separated organic layer was dried with anhydrous MgSO$_4$. The aqueous layer was extracted with dichloromethane and the liquid extract was dried with anhydrous MgSO$_4$. These two organic layers were joined together and concentrated. Then, the residue (10.98 g) was distilled at a bath temperature of 40 to 120° C. under reduced pressure of 5 mmHg, and the thus obtained fraction was subjected to silica gel column chromatography, using n-hexane as a mobile phase, whereby 4.05 g of methyl ester of α,α-bis-(trifluoromethyl)-p-isobutylphenylacetic acid was obtained (yield: 59%).

Infrared absorption spectrum: 1790 cm$^{-1}$ (C=O)

$^{19}$F-NMR (TFA, CH$_2$Cl$_2$): −3.2 ppm (s)

$^1$H-NMR (TMS, CDCl$_3$): 0.87 ppm (d, J=7.2 Hz, 6H)

1.35 to 2.34 ppm (m, 1H)

2.43 ppm (d, J=6.3 Hz, 2H)

3.81 ppm (s, 3H)

7.02 ppm (s, 4H)

EXAMPLE 4

1.28 g (0.01 mole) of naphthalene, 50 ml of dry dichloromethane and 2.28 g (0.01 mole) of perfluoro(2-methyl-1,2-epoxypropyl) methyl ether were charged into a three-necked flask having a capacity of 100 ml, provided with a stirrer and a dropping funnel, and the flask was cooled to 0° C. Then, 1.23 ml of BF$_3$·Et$_2$O was added into the flask with stirring.

Reaction was carried out at 45° C. for 24 hours while stirring, and then the reaction mixture was poured into ice water, and the separated organic layer was dried with anhydrous MgSO$_4$. The aqueous layer was extracted with dichloromethane and the liquid extract was dried with anhydrous MgSO$_4$. These two organic layers were joined together and concentrated, and then the residue (2.86 g) was sublimated at a bath temperature of 60° to 120° C. under reduced pressure of 20 mmHg, whereby 1.47 g of the sublimate was obtained. The sublimate was then subjected to silica gel column chromatography, using n-hexane/dichloromethane as a mobile phase, whereby 0.84 g of methyl ester of α,α-bis(trifluoromethyl)naphthylacetic acid was obtained (yield: 25%).

Infrared absorption spectrum: 1800 cm$^{-1}$ (C=O)

$^{19}$F-NMR (TFA, CH$_2$ Cl$_2$): −5.3 ppm (s)

$^1$H-NMR (TMS, CDCl$_3$):

3.82 ppm (s, 3H)

6.90 to 8.20 ppm (m, 7H)

EXAMPLE 5

0.67 g (0.01 mole) of pyrrole was charged into a three-necked flask having a capacity of 10 ml, provided with a stirrer and a dropping funnel, and the flask was cooled to 0° C.. Then, 2.28 g (0.01 mole) of perfluoro(2-methyl-1,2-epoxypropyl) methyl ether was dropwise added into the flask with stirring. After the dropwise addition, dichloromethane and water were added thereto with stirring and in that state the aqueous layer was neutralized with sodium hydrogen carbonate. The separated organic layer was dried with anhydrous MgSO$_4$. These two organic layers were joined together and concentrated, and the residue (0.97 g) was subjected to silica gel column chromatography, using n-hexane as a mobile phase, whereby 0.3 g of methyl ester of α,α-bis(trifluoromethyl)-2-pyrrolylacetic acid was obtained (yield: 10%).

Infrared absorption spectrum:

1740 cm$^{-1}$ (C=O)

3435 cm$^{-1}$ (NH)

$^{19}$F-NMR (TFA, CH$_2$Cl$_2$): −1.0 ppm (s)

$^1$H-NMR (TMS, CDCl$_3$):

3.46 ppm (s, 3H)

6.05 to 7.14 ppm (m, 3H)

7.76 to 9.34 ppm (br, 1H)

REFERENCE EXAMPLE 2.9 g (10 millimole) of methyl ester of α,α-bis(trifluoromethyl)phenylacetic acid, 2.5 g (63 millimole) of sodium hydroxide, 3.0 g of water and 3.0 ml of methanol were charged into an eggplant-type flask having a capacity of 100 ml, provided with a marine-type condenser and refluxed at a bath temperature of 90° C. for 6 hours. Methanol was distilled off from the reaction mixture under reduced pressure, and the residue was dissolved in 30 ml of 3N hydrochloric acid and then extracted with ether. The ether layer was dried with anhydrous MgSO$_4$ and then concentrated under reduced pressure. The thus obtained residue was subjected to silica gel column chromatography, using n-hexane/dichloromethane as a mobile phase, whereby 1.26 g of α-(trifluoromethyl)phenylacetic acid was obtained (yield: 62%).

Infrared absorption spectrum:

3210 cm$^{-1}$ (OH)

1720 cm$^{-1}$ (C=O)

$^{19}$F-NMR (TFA, CH$_2$Cl$_2$): −1.29 ppm (d, J=7.6 HZ)

$^1$H-NMR (TMS, CDCl$_3$): 4.26 ppm (q, 1H, J=7.2 HZ, methine-H)

7.28 ppm (s, 5H, ph)

11.9 ppm (br, 1H, OH)

Mass spectrum (CI, M/Z): 205(M$^+$+1)

What is claimed is:

1. A process for producing α,α-bis(trifluoromethyl) arylacetic acid ester represented by the following general formula:

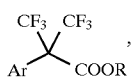

wherein Ar is an aryl group and R is a lower alkyl group, an aryl group or a benzyl group, which comprises allowing a perfluoro(2-methyl-1,2-epoxypropyl)ether compound, represented by the following general formula:

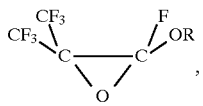

wherein R has the same meaning as defined above, to react with an aromatic compound represented by the following general formula:

ArH wherein Ar has the same meaning as defined above.

2. A process according to claim 1, wherein the aromatic compound is an aromatic hydrocarbon or its lower alkyl- or halogen-substituted compound.

3. A process according to claim 2, wherein the reaction is carried out in the presence of a Lewis acid catalyst.

4. A process according to claim 1, wherein the aromatic compound is an aromatic heterocyclic compound or its lower alkyl or halogen-substituted compound.

5. A perfluoro(2-methyl-1,2-epoxypropyl)ether compound represented by the following general formula:

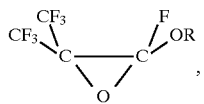

wherein R is a lower alkyl group, an aryl group or a benzyl group.

6. A process for producing a perfluoro(2-methyl-1,2-epoxy-propyl)ether compound represented by the following general formula:

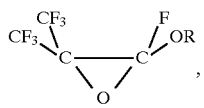

wherein R is a lower alkyl group, an aryl group or a benzyl group, which comprises oxidizing a heptafluoroisobutenyl ether compound represented by the following general formula:

$(CF_3)_2 C=CF(OR)$ wherein R has the same meaning as defined above, with ozone.

7. A process according to claim 6, wherein the oxidation with ozone is carried out with ozone-containing oxygen or air.

* * * * *